United States Patent [19]

Suzuki et al.

[11] Patent Number: 5,889,153
[45] Date of Patent: Mar. 30, 1999

[54] PROTEIN OR POLYPEPTIDE, METHOD FOR PRODUCING THE SAME AND INTERMEDIATE COMPOUND THEREFOR

[75] Inventors: Yosuke Suzuki; Syuji Sato, both of Ibaraki, Japan

[73] Assignee: Hisamitsu Pharmaceutical Co., Inc., Saga, Japan

[21] Appl. No.: 737,820

[22] PCT Filed: May 19, 1995

[86] PCT No.: PCT/JP95/00968

§ 371 Date: Mar. 14, 1997

§ 102(e) Date: Mar. 14, 1997

[87] PCT Pub. No.: WO95/32219

PCT Pub. Date: Nov. 30, 1995

[30] Foreign Application Priority Data

May 20, 1994 [JP] Japan ..................................... 6-107301

[51] Int. Cl.⁶ ...................... A61K 39/385; A61K 38/00; C07K 5/00; C07K 17/00
[52] U.S. Cl. ........................... 530/350; 530/324; 514/12; 436/71; 552/544
[58] Field of Search .................... 530/324, 350; 514/12; 424/193.1, 195.11; 436/71; 552/544

[56] References Cited

U.S. PATENT DOCUMENTS 4,179,337  12/1979  Davis et al. ............................ 435/181
5,359,030  10/1994  Ekwuribe ................................ 530/303
5,468,478  11/1995  Saifer et al. .......................... 424/78.27

OTHER PUBLICATIONS

Abuchowski et al, Journal of Biology Chemistry, vol. 252, No. 11, 1977.

*Primary Examiner*—Cecilia J. Tsang
*Assistant Examiner*—S. G. Marshall
*Attorney, Agent, or Firm*—Wenderoth, Lind & Ponack, L.L.P.

[57] ABSTRACT

The present invention provides a protein or polypeptide substance having at least one amino group bonded to a polyethyleneglycolosy group represented by the following general formula;

$$R_1-(OCH_2\,CH_2)_n-O-$$

(wherein $R_1$ represents an optionally substituted cholesteryl group; and n represents a positive integer which is arbitrarily variable), and a method for producing said the protein or polypeptide.

The present invention also provides a reactive polyethyleneglycol derivative as an intermediated for above the method.

The chemically modified protein or polypeptide of the present invention never impairs bonding with a receptor and has a high plysiological activity. Then, a behaviors in vivo of these substance is improved. Now medical substances or drugs having a high pharmacological activity can be developed by using these substance.

12 Claims, 5 Drawing Sheets

PROTEIN OR POLYPEPTIDE, METHOD FOR PRODUCING THE SAME AND INTERMEDIATE COMPOUND THEREFOR

This is a national stage application of PCT/JP95/00968 filed May 19, 1995.

BACKGROUND OF THE INVENTION

1. Field of the Invention

The present invention relates to a novel protein or polypeptide modified in bonding with a polyethylene glycol derivative, which is useful as a physiologically active or medically active substance or an intermediate compound therefor, and a method for producing the same. The present invention also relates a reactive polyethylene glycol derivative which is an intermediate compound for the novel protein or polypeptide above-mentioned.

2. Description of the Related Art

Many protein, polyaminoacid and peptide substances having a physiological or medical activity have recently been discovered, permitting expectation of more common application to medical substance. However, these protein and peptide substances have only a short half-life in blood when administered in vivo, giving a sufficient pharmacological effect in few cases. In order to utilize these substances as medical substance, therefore, it is believed to be absolutely necessary to improve behaviors in vivo by some method or other.

It is known that many of physiologically active or medically active substances administered in vivo, particularly into the blood flow, disappear from the biological body through glomerular filtration in the kidney. This glomerular filtration process may be considered a kind of molecular sieve in principle: substances of a molecular weight smaller than that of albumin (about 60,000) which is plasma protein indispensable for a biological body are excreted as a rule. In order to improve in vivo behaviors of protein and peptide medical substance disappearing from the body through glomerular filtration, therefore, it has conventionally been believed to be necessary to increase the molecular weight of medical substance through various chemical modifications.

As a method for improving behaviors in vivo of a protein or peptide medical substance, chemical modification using a water-soluble polymer typically represented by polyethylene glycol (hereinafter abbreviated as "PEG" as required) has popularly been applied. PEG has rather a long history: this substance has been utilized and studied widely in various areas since its synthesis in 1859. In the areas of biochemistry and medicines or medical drugs as well, it is confirmed that PEG exerts no interaction to protein except for physical stereo-hindrances, and no change is observed in protein CD spectrum even in a high-concentration aqueous PEG solution. This suggests that modification with PEG does not destroy the higher-order structure of protein. When, for example, PEG of a molecular weight of 4000 is administered to a dog at a rate of 90 mg/kg/day for a period of a year, no abnormality is observed in body weight or in a pathological or hemological inspection. Administration of PEG to a guinea pig does not cause an allergic symptom. Safety of PEG is thus commonly confirmed. By modifying protein with PEG having the unique properties as described above, it is expected to be possible to develop a protein or peptide medical substance having a long life in vivo, which is hard to be recognized not only by the immune system but also by the reticuloendothelial system.

When modifying a protein or peptide medical substance with PEG, the following advantages are available. When non-denatured protein is insoluble under a physiological pH condition or only partially soluble, it is possible to considerably improve solubility under the physiological pH condition by modifying protein with PEG, and also to reduce immune response of non-denatured protein. For these advantages, many types of protein or peptide medical substance have been modified with PEG to date for utilization in medical drugs [regarding general remarks, see Inada, Y., Yoshimoto, T., Matsushima, A. and Saito, Y. (1986) Trends Biotechno, 1, 4: 68–73].

PEG derivatives so far used for modifying protein or peptide medical substance include: 2-(alkoxypolyethyleneglycoxy)-4,6-dechlorotriadine [Abuchowski, A., Van Es, T., Palczuk, N. C. and Davis, F. F. (1977) J. Biol. Chem. 252, 3578–3581]; 6-(alkoxypolyethyleneglycoxy)-S-carboxamide-methyl-dithiocarbonate [King, T. P. and Weiner, C. (1980) Int. J. Peptide Protein Res. 16, 147–155]; 2-(alkoxypolyethyleneglycoxy)-N-succinimyzilsuccinate [Abuchowski, A, Kazo, G. M., Verhoest, C., Van Es, T., Kafkewitz, D., Viau, A. and Davis, F. (1984) Cancer Biochem. Biophys. 7, 175–186]; 2-(alkoxypolyethyleneglycoxy) carboxyimidazole [Beauchamp, C. O., Gonias, S. L., Menapace, D. P. and Pizzo, S. V. (1983) Anal. Biochem. 131, 25–33]; 2-alkoxypolyethyleneglycoxy)-2,4,5-trichlorobenzene [Versonese, F. M., Largajolli, R., Boccu, E., Benassi, C. A. arid Schiavon, O. (1985) Applied Biochem. Biotech., 11, 141–152]; 2-(alkoxypolyethylene-glycoxy)-4-nitrobenzene [Versonese, F. M., Largajolli, R., Boccu, E., Benassi, C. A. and Schiavon, O. (1985) Applied Biochem. Biotech. 11, 141–152]; 2-(alokxypolyethylene-glycoxy)-2,2,2-trifluoroethane [Delgads, C., Patel, J. N., Francis, G. B. and Fisher, D. (1990) Biotech. Applied Biochem. 12, 119–128]; 2-(alkoxypolyethylenealdehyde) [Andrews, B. A., Head, D. M., Dunthrone, P. and Asenjo, J. A. (1990) Biotech. Tech. 4, 49–54]; and 2-alkoxypolyethylene-glycoxymethylepoxide [Andrews, B. A., Head, D. M., Dunthrone, P. and Adenjo, J. A. (1990) Biotech. Tech. 4, 49–54].

Regarding modification with a PEG derivative, a number of patent applications have been filed to date. Some examples include, for example, Japanese Provisonal Patent Publication JP-A-61-178,926; Japanese Provisional Patent Publication JP-A-61-249,388; Japanese Provisional Patent Publication JP-A-1-316,400; Japanese Provisional Patent Publication JP-A-2-117,920; Japanese Provisional Patent Publication JP-A-3-88,822; Japanese Proisional Patent Publication JP-A-5-117,300; Japanese Provisional Patent Publication JP-A-132,431; Japanese Provisional Patent Publication JP-A-5-214,092; and Japanese Provisional Patent Publication JP-A-5-503,092. All these inventions are based on attention to the high water solubility of PEG, having therefore a terminal structure comprising a short-chain aliphatic group.

However, the method of improving behaviors in vivo by increasing the molecular weight of a protein or peptide medical substance through PEG modification is considered to suffer on the other hand limitations imposed on medical substances to which it is applicable. For example, most of conventional protein or peptide medical substances of which PEG modification has been confirmed to have improved behaviors in vivo and increased pharmacological effect are limited to enzymes. A conceivable cause is the pharmacological effect expressing mechanism unique to enzymes.

An enzyme having a physiological activity expresses its effect by causing a substance detrimental for a biological body or a substance specifically required at a site suffering from a disease such as tumor to specifically disappear through a chemical reaction such as metabolism. In the case of PEG modification of an enzyme, therefore, it is possible to increase the pharmacological effect by only causing enzyme molecules to be present in blood for a long period of time. However, such a method of increasing the molecular weight of a medical substance through PEG modification is not clearly a method commonly applicable to all protein or peptide medical substance other than enzymes.

More particularly, a protein or peptide medical substances requiring improvement of behaviors in vivo necessitates bonding with a receptor, for example, for the purpose of displaying its pharmacological effect, PEG modification cannot be expected to increase the pharmacological effect, but the pharmacological effect decreases in many cases as a result of impairment of receptor bonding caused by stress hindrance of polymer PEG used for modification. For example, in Ehrat, M, and Luisi, P. L. (1983) Biopolymer 22, 569, 573, when PEG-modifying insulins to be bonded with a receptor for more remarkable pharmacological effect, a decrease in pharmacological effect in vivo by up to 50% is reported as compared with non-modified insulin.

Therefore, for many of protein, polyaminoacid and peptide substances expected to become applicable to medical uses, bonding with a receptor or the like is a necessary prerequisite for the expression of pharmacological effect. Under such circumstances, there is an increasing demand for achievement of a novel method of improving behaviors in vivo of medical substances, which does not impair bonding with a site where a pharmacological effect is to be expressed, such as a receptor or the like, i.e., novel means for chemical modification, and a medical substance comprising a pharmacologically active substance modified by such means.

SUMMARY OF THE INVENTION

The present invention has therefore an object to provide a novel chemically-modified physiologically active or medically active substance which never impairs bonding with a receptor or the like, a medical substance comprising the same, and novel means of modification for such substance and medical drug.

The present invention provides:

(a) A protein or polypeptide substance polyethyleneglycoloxy group represented by the following general formula:

(wherein, $R_1$ represents an optionally substituted cholesteryl group; and n represents a positive integer which is arbitrarily variable);

(b) A method for producing a protein or peptide substance having least one amino group bonded to a polyethyleneglycoloxy group represented by the following general formula:

, comprising the step of causing a reaction of the protein or peptide substance with a reactive polyethyleneglycol derivative represented by the following general formula:

[wherein, $R_1$ represents an optionally substituted cholesteryl group; $R_2$ represents any of the following formulae (a), (b) and (c):

(wherein, $R_3$ represents OH, alkoxy group, acyloxy group, a halogen atom or $R_1$—$(OCH_2CH_2)_n$—O—); and n represents a positive integer which is arbitrarily variable]; and (c) A polyethylenglycol derivative represented by the following general formula:

[wherein, $R_1$ represents an optionally substituted cholesteryl group; $R_2$ represents any of the following formulae (a), (b) and (c):

(wherein, $R_3$ represents OH, alkoxy group, acyloxy group, a halogen atom or $R_1$—$(OCH_2CH_2)_n$—O—); and n represents a positive integer which is arbitrarily variable)].

More specifically, the present invention was derived from studies on a novel PEG derivative for improving in-vivo behaviors of protein, polyaminoacid and polypeptide substances having a physiological or medical activity. The present invention was completed on the basis of findings that, when using the novel PEG derivative having a terminal of the cholesterol structure, an interaction with polymer components in blood is achieved, and this improves the in-vivo behaviors of a medical substance. The present invention makes it possible to solve bonding hindrance between a medical substance and a receptor or the like, which is a problem in conventional PEG modification of a protein or peptide medical substance, and to develop a medical substance exhibiting a high pharmacological activity.

DESCRIPTION OF THE PREFERRED EMBODIMENT

The protein or peptide substance of the present invention is produced by bonding a reactive PEG derivative having a cholesterol structure as described above at a terminal and a modifier comprising a physiologically active substance.

Regarding the general formula, $R_1$ in the polyethyleneglycoloxy group represents a cholesteryl group which may have an arbitrary substituent so far as it does not impair chemical modification action. Appropriate substituents include, for example, alkyl group, alkenyl group, hydroxyl group and alkoxyl group.

$R_2$ bonded to this polyethyleneglycoloxy group may have any of the partial structures of $R_3$ as described above, and the halogen atom in $R_3$ means chlorine, bromine, iodine or the like. $R_3$ may be OH, alkoxy group or acyloxy group. In the formula, n represents a positive integer which is arbitrarily variable, and should be up to about 500, or preferably up to 200, or more preferably, within a range of from about 10 to 100.

Now, the method for producing the foregoing protein or polypeptide substance modified with the foregoing PEG derivative of the present invention is described. It suffices to cause a reaction between a ratio of the protein or polypeptide substance of 1 mol and a ratio of the reactive PEG derivative according to the following formula of 1 mol or over:

$$R_1-(OCH_2CH_2)_n-O-R_2$$

There is no particular limitation on the reaction solvent so far as it does not participate in the reaction. Preferable solvents include, for example, phosphoric acid buffer solution, boric acid buffer solution, Tris. acid buffer solution and acetic acid buffer solution. An organic solvent such as acetonitrile, dimethylsulfoxide, and dimethylformamide, which do not participate in the reaction without deactivating a protein or polypeptide substance may be added. Any of the foregoing reactive PEG derivative and the protein or polypeptide substance may be added first to the reaction solvent, or may be added simultaneously.

The reaction may be caused without adding a reaction solvent.

The reaction temperature may be at any level so far as it does not cause denaturation of the protein or polypeptide substance, and should preferably be within a range of from about 0° to 40° C.

A reaction time within a range of from about 0.5 to 72 hours is sufficient, and a time within a range of from about 1 to 24 hours is usually sufficient to cause progress of the reaction.

After the reaction, the reaction product is purified by an ordinary method for purifying a protein or polypeptide substance such as dialysis, salting-out, ultrafiltration, ion-exchange chromatography or electrophoresis, thereby obtaining a chemically modified protein or polypeptide target substance. The extent of modification of amino group can be confirmed by an amino acid analysis carried out, for example, after acid decomposition.

The foregoing reactive PEG derivative can be manufactured with a polyethyleneglycol monocholesterol (hereinafter abbreviated as "C-PEG derivative") available by causing polyethyleneoxide to react with tertiary hydroxyl group present in cholestrine (also known as cholesterol) as the starting material.

A commercially available product (eg., one made by Nihon Emulsion Company) or a synthesis product thereof may be used as C-PEG.

More particularly, a C-PEG derivative is first dissolved or suspended in an organic solvent such as acetonitrile, toluene, xylene, benzene, tetrahydrofuran, dioxane, dimethylsulfoxide or dimethylformamide, which may be any solvent so far as it does not participate in the reaction, and subsequently, any of the compounds expressed by the following general formulae (a), (b) and (c) is caused to react with the resultant solution or suspension in an amount of 1 mol or over relative to 1 mol of the C-PEG derivative:

(a)

(b)

(c)

[where, X represents a halogen atom such as chlorine, bromine or iodine.]

An organic basic catalyst such as trimethylamine or triethylamine may be added in an amount of 1 mol relative to 1 mol of the C-PEG derivative.

An inorganic base such as sodium hydroxide, potassium hydroxide or anhydrous sodium carbonate may be used: in this case, hydrogen in the hydroxide group of the C-PEG derivative is first substituted with sodium in the foregoing solvent, together with the C-PEG derivative, and then, any of the compounds of the above-mentioned general formulae (a), (b) and (c) is added for reaction.

The reaction temperature should preferably be within a range of from about 0° to 300° C. or more preferably, from about 10° to 150° C.

The reaction temperature may be within a range of from several minutes to 24 hours.

The produced compound is purified by an ordinary chemical treatment such as extraction, concentration, recrystallization, reprecipitation, column chromatography, or distillation, thereby obtaining the foregoing reactive PEG derivative.

The water-soluble PEG derivative should preferably be selected from polyethyleneglycol and homopolymers of polyethyleneglycol having a hydroxide group in the structure thereof, or more preferably, from water-soluble polymers such as polyethyleneglycol and derivative thereof.

The water-soluble PEG derivative used in the present invention should preferably have a molecular weight within a range of from 100 to 100,000, although there is no particular restrictions, or more preferably, from 500 to 10,000.

In the present invention, the modified portion of the protein or peptide substance to be modified by the PEG derivative having a terminal of the cholesterol structure should preferably be an amino group, particularly a primary amino group.

Regarding the physiologically active substance modified by the PEG derivative having the cholesterol structure at the terminal thereof, there is no particular limitation imposed on the kind thereof in the present invention. Particularly for a protein or peptide medical substance, preferable substances include, for example, substances P (hypothalamic hormone); corticotropin, lipotropin, melanotropin, vasopressin (neurohypophysial hormone), parathyroid hormone (thyroid hormone); thymopetine (thymus hormone); insulin, glucagon (pancreas hormone); nerve growth factor, epidermal growth factor, insulin-like growth factor, human transforming/growth factor, growth hormone-releasing factor, i.e., CRF, fibroblast growth factor (growth factor); secretin, cholecystokinin, vasoactive intestinal polypeptide, motilin (gastrointestinal hormone); gonadotropin (ciliary hormone); gonadotropic hormone-releasing hormone (gonadotropic hormone); relaxin (ovarian hormone); blood coagulation factor i-factor and u-factor (hemophilia factor); streptokinase, fibrinolysin, deoxyribonuclease, superoxide dismutase (hereinafter abbreviated as "SOD"), bilirubin oxidase, elastase, asparaginase (enzyme); tissue plasminogen activator, i.e., t-PA, urokinase (plasminogen); lymphokine (eg., interleukin), interferon, granulocyte colony-stimulating factor, i.e., G-CSF, macrophage colony-stimulating factor, i.e., M-CSF, granulocyte macrophage colony-stimulating factor, i.e., GM-CSF (stimulating factor); erythropoietin (hematopoietic factor), calcitonin, calcitonin gene-related peptide (Ca-regulatory hormone); atrial natriuretic peptide (diuretic hormone); monoclonal and polyclonal antibodies; immunogen; enzyme-inhibiting factor; various polyamino acids including poly-L-lysine and poly-D-lysine; virus-derived cell membrane fusing peptides; suhistone, protamine )gene binding protein) and analog-structured substances having a physiological activity similar to that of the foregoing protein or peptide drugs. These protein or peptide drugs may be formed by macerating from a natural source or cells subjected to a genetic engineering treatment, or through any of various in-vitro synthetic methods. The terms in parentheses in the above-enumerated examples show main uses of the protein or peptide medical substances. It is needless to mention that the protein or peptide substances used in the present invention include various amino acids generically called polyaminoacids.

In the present invention, the number of modified points in the physiologically active substance to be modified by the PEG derivative having the cholesterol structure at the terminal thereof, though not particularly limited, should preferably be within a range of from 1 to 100, or more preferably, from 1 to 10.

In the present invention, the protein or peptide substances are modified by the use of the reactive PEG derivative having the specific chemical structure as described above, whereby the in-vivo behaviors of these medical substances having a high physiological activity are effectively improved without impairing bonding with a receptor or the like.

EXAMPLES

Now, the features and effects of the present invention will be described further in detail by means of examples.

Example 1

[Synthesis of a novel PEG derivative having the cholesterol structure at the terminal thereof (polyethyleneglycol-monocholesterolether)]

(1)

After dissolving polyethyleneglycol-monocholesterolether (n=10, average molecular weight: 800, 9.5 g) and p-nitrophenyl chloroformate (0.6 g) in toluene (59 ml), triethylamine (0.3 g) was added, and the mixture was stirred at the room temperature for 18 hours. Precipitated impurities were filtered off and the filtrate was concentrated under reduced pressure. The resultant residue was purified through a silica gel column, thereby obtaining p-nitrophenyl formate-activated polyethyleneglycolmonocholesterolether (compound A) in an amount of 7.1 g (yield: 75%).

Melting point: 23° C.

Elemental analysis: $C_{54}H_{31}NO_{15}$

TABLE 1

|  | C | H | N |
| --- | --- | --- | --- |
| Calculated | 65.23 | 9.23 | 1.41 |
| Measured | 65.15 | 9.46 | 1.38 |

(2)

Polyethyleneglycol-monocholesterolether (n=20, average molecular weight: 1,200, 6.0 g), succinic anhydride (0.6 g) and pyridine (0.5 ml) were dissolved in dichloromethane (30 ml) and circulated for three days. Subsequently, precipitated impurities were filtered off, and the filtrate was evaporated. After dissolving the resultant residue in distilled water (50 ml), extraction was conducted with chloroform (50 ml), and the resultant organic layer was evaporated, thereby obtaining poly-ethyleneglycol-monocholesterolether succinate ester. Then, the resultant polyethyleneglycolmonocholesterolether succinate ester and N-succinimide (0.6 g) were dissolved in dimethylformamide (100 ml). After cooling the reaction system to 0° C., dichlorohexylcarbodiimide (0.7 g) dissolved in dimethylformamide (5 ml) was dripped and stirring was continued at room temperature for 24 hours. The precipitated impurities were filtered off and the filtrate was concentrated under a reduced pressure. Then, the resultant residue was purified through a silica gel column, thereby obtaining N-succinimide-activated polyethyleneglycol-monocholesterolether (compound B) in an amount of 4.8 g (yield: 78%).

Melting point: 33° C.
Elemental analysis: $C_{75}H_{135}NO_{26}$

TABLE 2

|  | C | H | N |
|---|---|---|---|
| Calculated | 61.41 | 9.28 | 0.95 |
| Measured | 61.29 | 9.69 | 0.88 |

(3)

After dissolving polyethyleneglycol-monocholesterolether (n=30, average molecular weight: 1,700, 4.5 g) and p-nitrophenylchloroformate (0.6 g) in toluene (50 ml), triethylamine (0.3 g) was added, and the mixture was stirred at the room temperature for 18 hours. The precipitated impurities were filtered off and the filtrate was concentrated under a reduced pressure. The resultant residue was purified through a silica gel column, thereby obtaining p-nitrophenyl formate-activated polyethyleneglycol-monocholesterolether (compound C) in an amount of 3.8 g (yield: 81%).

Melting point: 36° C.
Elemental analysis: $C_{94}H_{171}NO_{39}$

TABLE 3

|  | C | H | N |
|---|---|---|---|
| Calculated | 58.21 | 8.89 | 0.72 |
| Measured | 58.12 | 8.95 | 0.68 |

(4)

After dissolving anhydrous sodium carbonate (2.5 g) and cyanulchloride (1.3 g) in benzene anhydride (100 ml), polyethyleneglycol-monocholesterolether (n=30, average molecular weight: 1,700, 4.5 g) was added, and the mixture was stirred at the room temperature for 24 hours. Then, triethylamine (0.3 g) was added, and the mixture was stirred at the room temperature for 18 hours. The precipitated impurities were filtered off, and the filtrate was concentrated under a reduced pressure. The resultant residue was purified through a silica gel column, thereby obtaining cyanulchloride-activated polyethylene-glycol-monocholesterolether (compound D) in an amount of 3.4 g (yield: 76%).

Melting point: 38° C.
Elemental analysis: $C_{90}H_{167}N_3O_{31}Cl_2$

TABLE 4

|  | C | H | N |
|---|---|---|---|
| Calculated | 58.17 | 9.06 | 2.26 |
| Measured | 58.05 | 9.11 | 2.15 |

(5)

After dissolving anhydrous sodium carbonate (2.5 g) and cyanulchloride (1.3 g) in benzene anhydride (100 ml), polyethyleneglycol-monocholesterolether (n=30, average molecular weight: 1,700, 9.0 g) was added, and the mixture was stirred at the room temperature for 24 hours. Then, triethylamine (0.3 g) was added, and the resultant mixed solution was further stirred at the room temperature for 18 hours. The precipitated impurities were filtered off, and the filtrate was concentrated under a reduced pressure. The resultant residue was purified through a silica gel column, thereby obtaining double-type cyanulchloride-activated polyethyleneglycol-monocholesterolether (compound E) in an amount of 5.8 g (yield: 63%).

Melting point: 37° C.
Elemental analysis: $C_{177}H_{334}N_3O_{62}Cl$

TABLE 5

|  | C | H | N |
|---|---|---|---|
| Calculated | 60.18 | 9.53 | 1.18 |
| Measured | 60.06 | 9.64 | 1.07 |

(6)

After dissolving polyethyleneglycol-monocholesterolether (n=100, average molecular weight: 4,700, 12.5 g) and p-nitrophenyl chloroformate (0.6 g) in toluene (50 ml), triethylamine (0.3 g) was added, and the mixture was stirred at the room temperature for 18 hours. The precipitated impurities were filtered off, and the filtrate was concentrated under a reduced pressure. The resultant residue was purified through a silica gel column, thereby obtaining p-nitrophenyl formate-activated polyethyleneglycol-monocholesterolether (compound F) in an amount of 9.8 g (yield: 78%).

Melting point: 45° C.
Elemental analysis: $C_{234}H_{451}NO_{105}$

TABLE 6

|  | C | H | N |
|---|---|---|---|
| Calculated | 56.67 | 9.16 | 0.28 |
| Measured | 56.54 | 9.25 | 0.21 |

Example 2

[Modification of insulin with novel PEG derivative]

After dissolving bovine-derived insulin (6.0 mg) in 0.025 mM $Na_2B_4O_7.10H_2O$ (pH: 9.2) in an amount of 200 ml, p-nitrophenyl formate-activated polyethyleneglycolmonocholesterolether (compound A), N-succinimide-activated polyethyleneglycol-monocholesterolether (compound B), p-nitrophenyl formate-activated polyethyleneglycol-monocholesterolether (compound C), cyanulchloride-activated polyethyleneglycol-monocholesterolether (compound D), double-type cyanulchloride-activated polyethyleneglycol-monocholesterolether (compound E), and p-nitrophenyl formate-activated polyethyleneglycol-monocholosterolether (compound F) obtained in Example 1 were respectively added in an amount of 2.0 nmol, and the mixtures were stirred at the room temperature for five hours. The resultant mixtures were purified through gel filtration by the use of Sephadex G-75 (made by Pharmacia Company). The target fraction was desalted and concentrated through ultrafiltration (made by Pharmacia Company), thereby obtaining the target aqueous solution (1.8 mg/ml). In the case of p-nitrophenyl formate-activated polyethylene-glycol-monocholesterolether (compoundA), the target modification was insufficient. This is attributable to the low water-solubility. In the case of p-nitrophenyl formate-activated polyethyleneglycol-monocholesterolether (compound F) also, the chemical modification was not sufficient. This is considered to be due to stereo-hindrance. In the other cases of PEG derivative-modified insulin, elution was observed in fractions corresponding to the molecular weight when a few points per molecule of insulin were modified.

Example 3

[Modification of SOD with novel PEG derivative]

After dissolving bovine-derived Cu, Zn—SOD (Superoxide Dismutase) (30 mg) in 0.025 mM $Na_2B_4O_7 \cdot 10H_2O$ (pH: 9.2) in an amount of 30 ml, 3.9 mg p-nitrophenyl formate-activated polyethyleneglycol-monocholesterolether (compound C) obtained in Example 3 were added, and the mixture was stirred at the room temperature for five hours. Then, the mixture was purified through gel filtration using Sephadex G-75 (made by Pharmacia Company). The target fraction was desalted and concentrated through ultrafiltration (made by Pharmacia Company), thereby obtaining a target aqueous solution (20.2 mg/ml).

Example 4

[In-vivo experiment on components in blood and interaction of novel PEG derivative-modified insulin]

Figure 1:
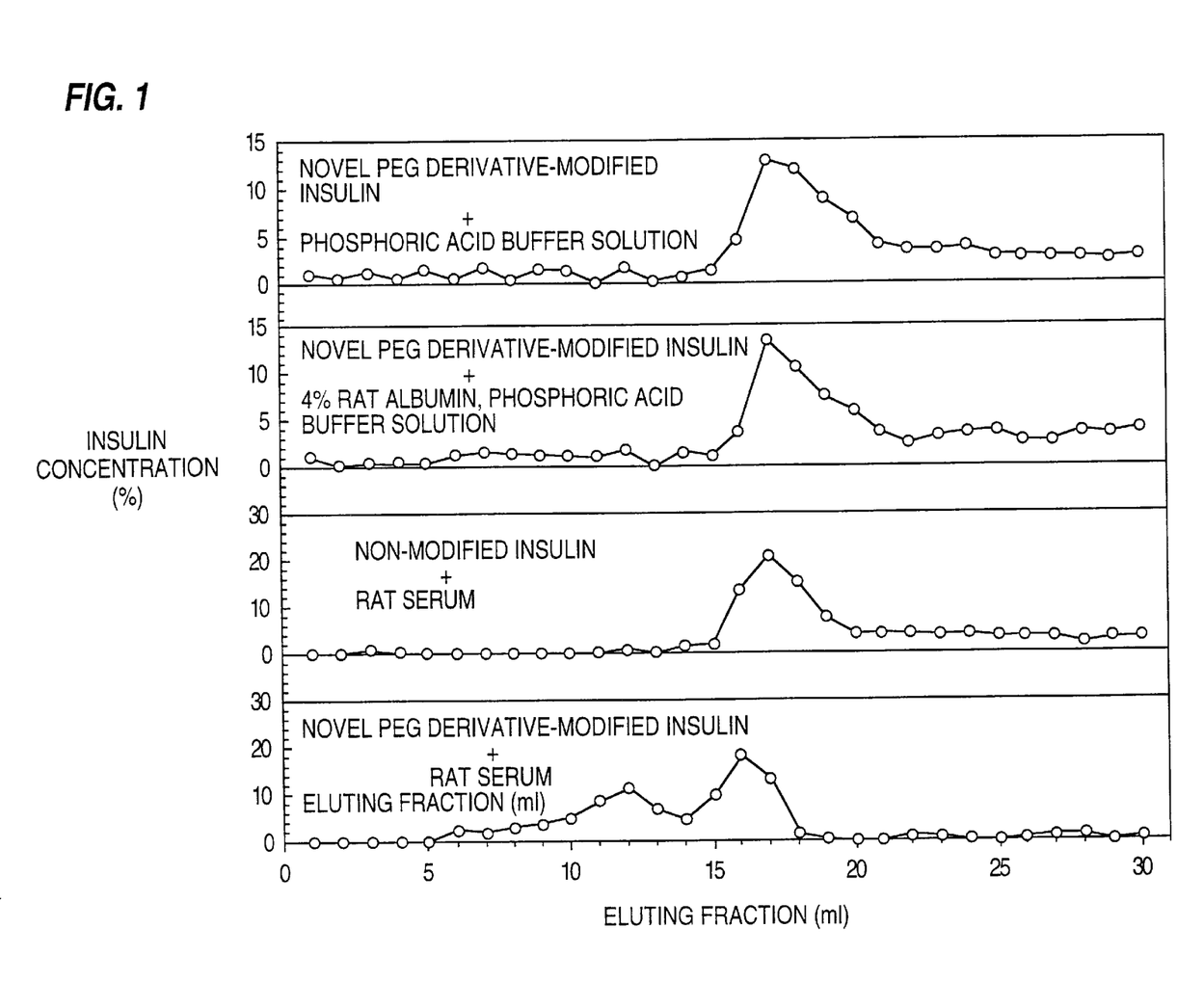
FIG. 1 shows a graph illustrating concentrations in blood of PEG-derivative-modified insulin and the result of an interaction in-vitro test.

Aqueous insulin solution, in an amount of 50 μl, modified with p-nitrophenyl-activated polyethyleneglycolmonocholesterolether (compound C) obtained in Example 2 was added to 450 μl serum taken from a Wister male rat or aqueous 4% rat albumin solution, and after stirring at 37° C. for 30 minutes, gel filtration-separation was conducted by the use of Sepharose 4B (made by Pharmacia Company). The result is shown in FIG. 1. An increase in the molecular weight of the novel PEG derivative-modified insulin was confirmed only in the case of mixing with rat serum, and the presence of interaction was confirmed with serum components other than albumin.

Example 5

[In-vivo experiment on components in blood and interaction of novel PEG derivative-modified SOD]

Figure 2:
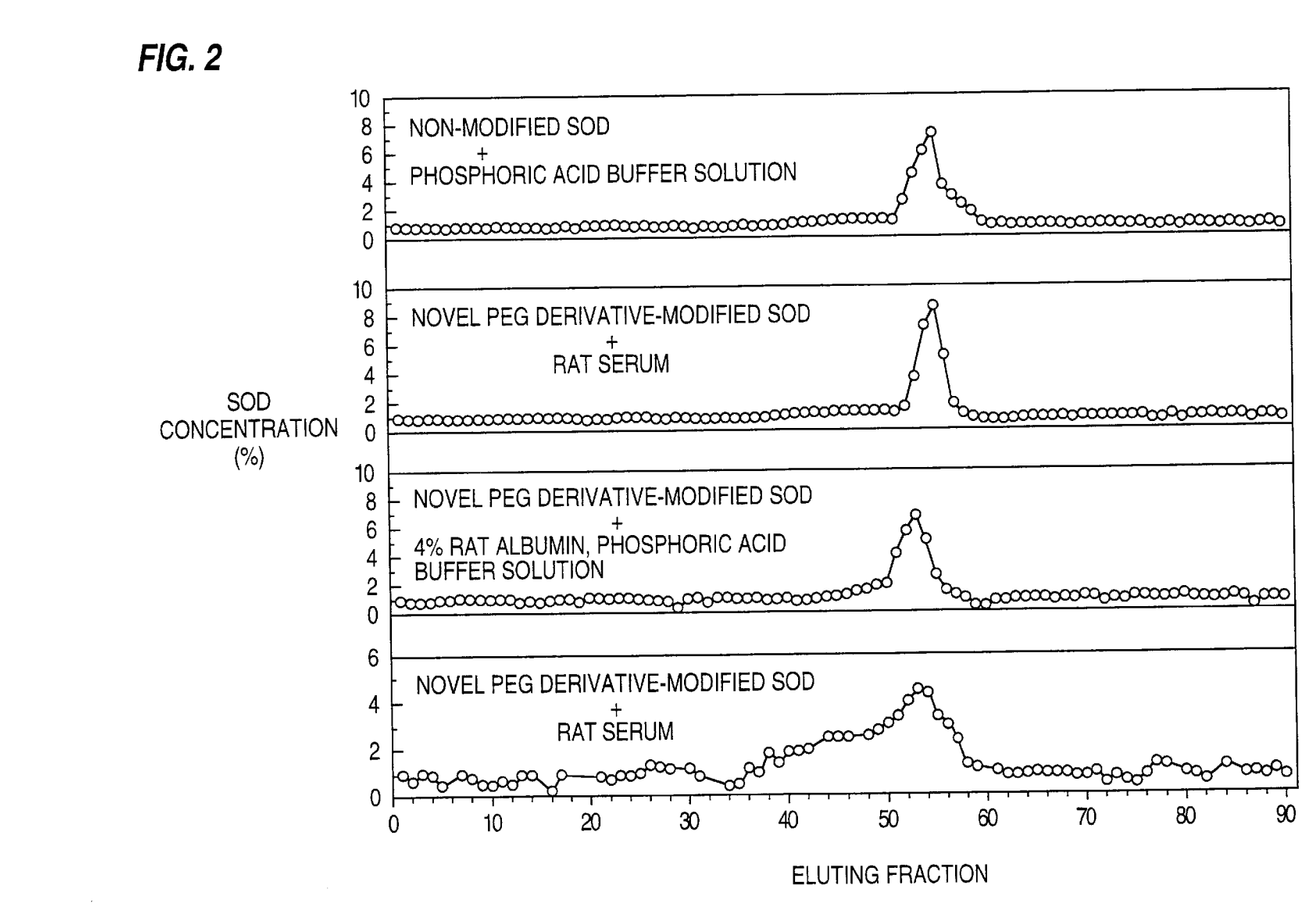
FIG. 2 shows a graph illustrating concentrations in blood of PEG-derivative-modified SOD and the result of an interaction in-vitro test.

Aqueous solution, in an amount of 50 μl, of SOD modified with p-nitrophenyl formate-activated polyethyleneglycolmonocholesterolether (compound C) obtained in Example 3 was added to 450 μl serum taken from a rat or 4% aqueous rat albumin solution, and after stirring at 37° C. for 30 minutes, the mixture was subjected to gel filtration-separation by the use of Sepharose 4B (made by Pharmacia Company). The result is shown in FIG. 2. An increase in the molecular weight of the novel PEG derivative-modified SOD was confirmed only in the case of mixing with rat serum, and the presence of interaction was confirmed with serum components other than albumin.

Example 6

[In-vivo experiment on in-vivo behaviors of insulin modified with novel PEG derivative]

Figure 3:
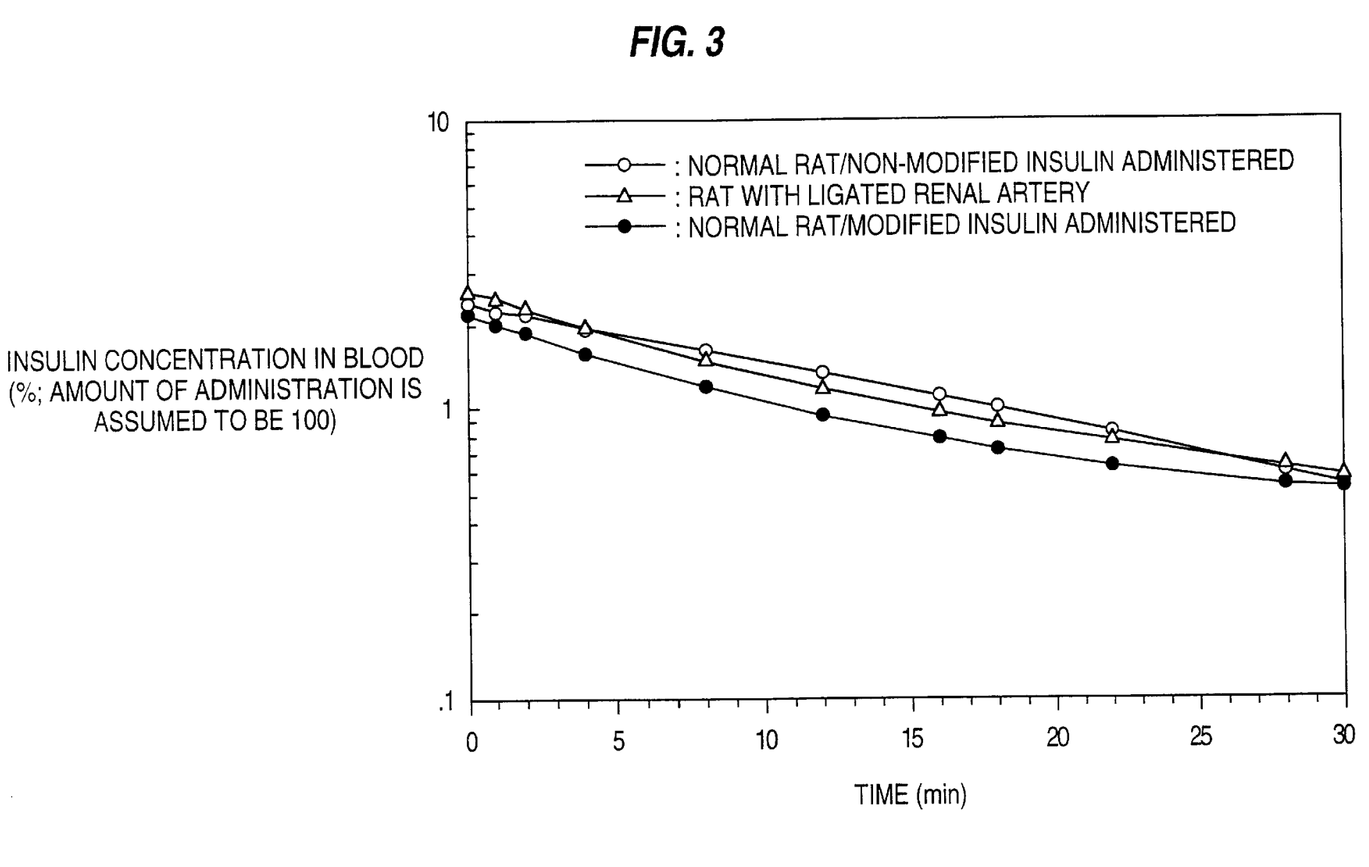
FIG. 3 shows a graph illustrating the result of an in-vivo test on behaviors in vivo of PEG-derivative-modified insulin.

About 0.5 U p-nitrophenyl formate-activated polyethyleneglycol-monocholesterolether (compound C)-modified or non-modified insulin were intravenously administered to an urethane-anesthetized rat or a rat of which only the renal artery was ligated after urethane anesthesia. Then, at prescribed intervals of time, venous blood was sampled to measure the insulin concentration in blood and blood glucose value at each time point. The result is shown in FIG. 3. The in-vivo behaviors of the modified and non-modified insulin in the normal rat were the same as the in-vivo behaviors of non-modified insulin in the rat having the ligated renal artery. This result suggests that, for the modified insulin, the interaction with a clearance receptor participating in disappearance from the biological body is not hindered by the modification. From the fact that, in the normal rat, the modified insulin and the non-modified insulin had identical pharmacological effects, it is confirmed that, in the novel PEG derivative-modified insulin, the interaction with the insulin receptor associated with the pharmacological functions participating in disappearance from the biological body is not impaired by the modification.

Example 7

[In-vivo experiment on in-vivo behaviors of novel PEG derivative-modified SOD]

Figure 4:
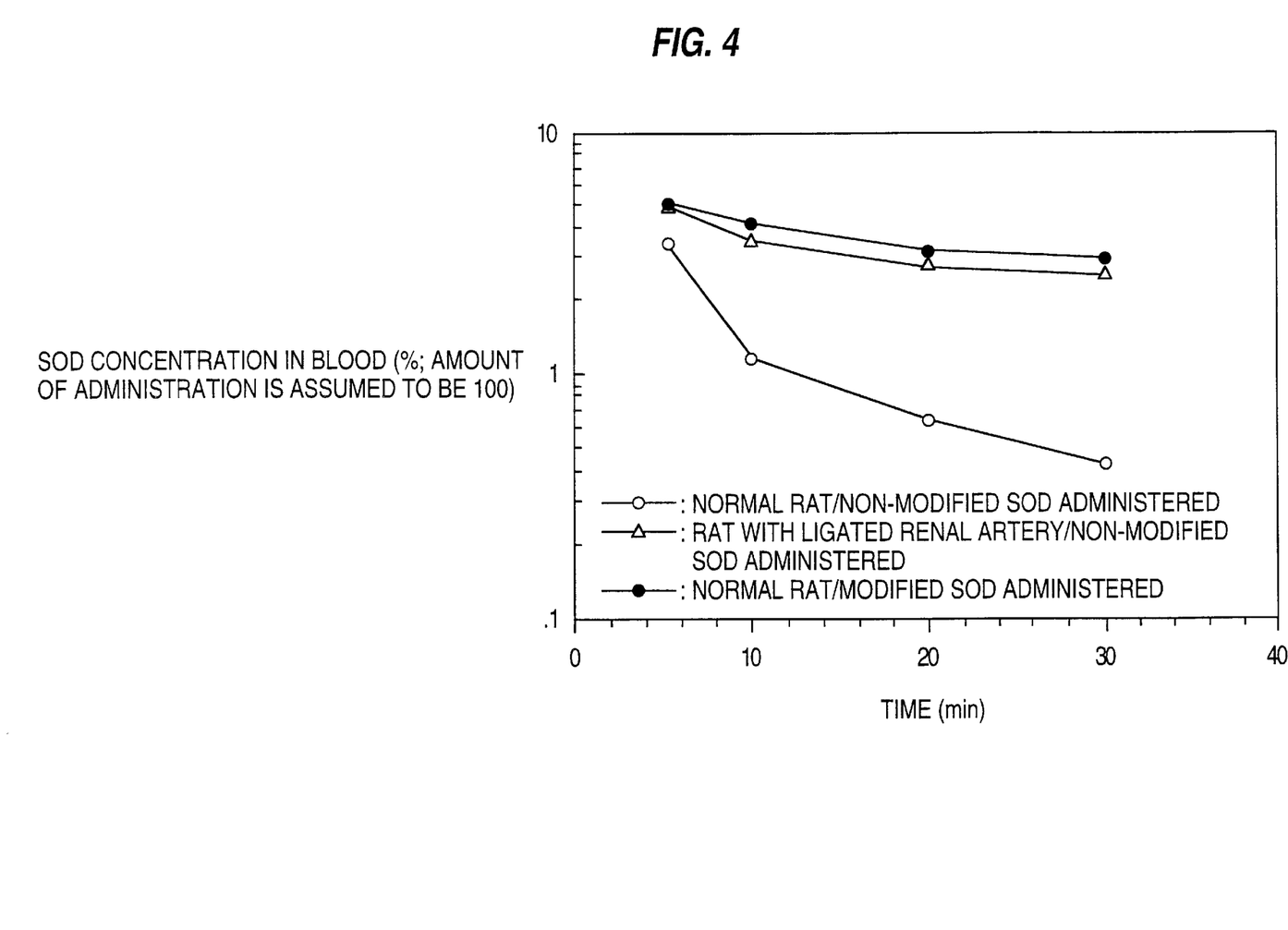
FIG. 4 shows a graph illustrating the result of an in-vivo test on behaviors in vivo of PEG-derivative-modified SOD.

About 5,000 U p-nitrophenyl formate-activated polyethyleneglycol-monocholesterolether (compound C)-modified or non-modified SOD were intravenously administered to an urethane-anesthetized rat or a rat of which only the renal artery was ligated after urethane anesthesia. Then, at prescribed intervals of time, venous blood was sampled to measure the SOD concentration in blood at each time point. The result is shown in FIG. 4. The result suggests that the in-vivo behaviors of the non-modified SOD in the normal rat are clearly improved, and glomerular filtration plays an important role in disappearance of non-modified SOD from the biological body. On the other hand, it is confirmed that the in-vivo behaviors of the modified SOD are largely improved: the half-life in blood is extended, and the interaction with components in blood caused by modification allows the modified SOD to be exempt from glomerular filtration.

Example 8

[In-vivo experiment on pharmacological effect of novel PEG derivative-modified SOD]

Figure 5:
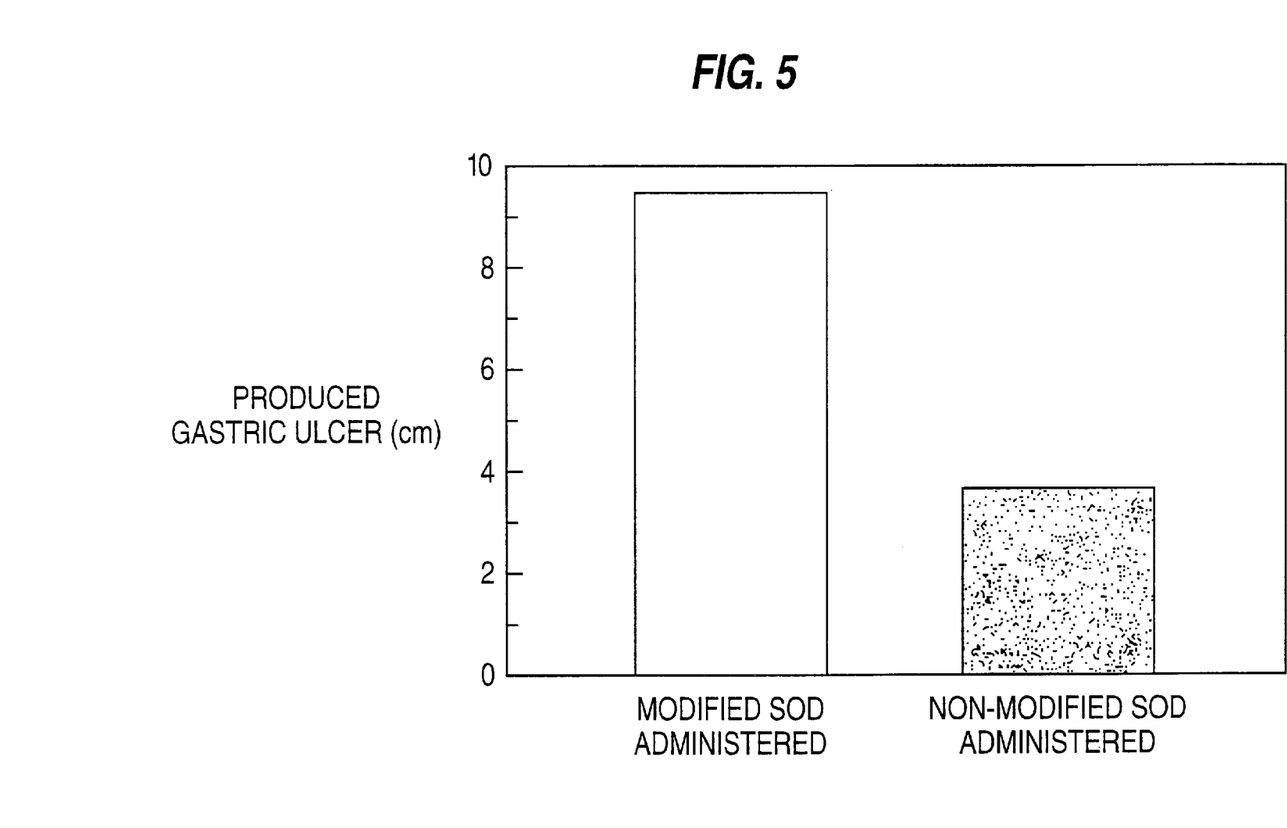
FIG. 5 shows a graph illustrating the result of an in-vivo test on pharmacological effect of PEG-derivative-modified SOD.

To a rat, 10,000 U p-nitrophenyl formate-activated polyethyleneglycol-monocholesterolether (compound C)-modified or non-modified SOD were administered. Then, an acute gastric ulcer was caused in accordance with the method for preparing a water immersion stress ulcerative model, and the effect inhibiting generation of ulcer at this point was investigated. The result is shown in FIG. 5. It is confirmed from this result that, in the case of administration of the modified SOD, as compared with administration of the non-modified SOD, production of an ulcer is inhibited, and the modification intensifies the pharmacological effect in vivo.

INDUSTRIAL APPLICABILITY

By using the PEG derivative of the present invention, in-vivo behaviors of physiologically active substance, particularly protein, polyaminoacid and polypeptide substances are improved, making it possible to develop medical substance exhibiting a high pharmacological effect, and at the same time, it becomes possible to improve water-solubility of these drugs, increase storage stability thereof, reduce immunogenicity, and improve resistance to enzymatic degradation.

The PEG derivative-modified protein or polypeptide substances of the present invention can be administered to mammals (such as dogs, pigs, cows, horses and persons), through oral or parenteral administration, in the form of tablets, capsules, injection and other medical compositions by using a known carrier or diluent.

Or, for example, the PEG derivative-modified insulin of the present invention has a function of reducing blood glucose, and can therefore be administered as an injection in an amount within a range of from 4 to 100 units per day as a treatment drug or a preventive agent against diabetes mellitus.

The peg derivative-modified sod, having an antiulcer effect, is applicable as an antiulcer agent against stomach or duodenum, or having an anti-inflammatory effect, is applicable as an anti-inflammatory agent, and can be administered in an amount of from 1 to 5 mg/kg per day in the form of tablets or injection.

What is claimed is:

1. A modified polypeptide comprising a polypeptide having an amino group bonded to a polyethyleneglycoloxy group represented by the following general formula:

wherein $R_1$ represents a cholesteryl group, and n represents a positive integer up to 500.

2. The modified polypeptide according to claim 1, wherein the polypeptide is insulin.

3. The modified polypeptide according to claim 1, wherein the polypeptide is superoxide dismutase.

4. A method for producing the modified polypeptide of claim 1, comprising the step of reacting the polypeptide with a reactive polyethyleneglycol represented by the following general formula:

wherein $R_1$ represents a cholesteryl group, n represents a positive integer up to 500, and $R_2$ represents any of the following formulae (a), (b) and (c):

wherein $R_3$ represents OH, alkoxy group, acyloxy group, a halogen atom or $R_1$—$(OCH_2CH_2)_n$—O—, wherein $R_1$ and n have the same meanings as defined above.

5. The method of claim 4, wherein the polypeptide is insulin or superoxide dismutase.

6. A reactive polyethyleneglycol derivative represented by the following general formula:

wherein $R_1$ represents a cholesteryl group, n represents a positive integer up to 500, and $R_2$ represents any of the following formulae (a), (b) and (c):

wherein $R_3$ represents OH, alkoxy group, acyloxy group, a halogen atom or $R_1$—$(OCH_2CH_2)_n$—O—, wherein $R_1$ and n have the same meanings as defined above.

7. A composition for the treatment of diabetes mellitus comprising the modified polypeptide of claim 2 and a pharmaceutically acceptable carrier or diluent.

8. A composition for the treatment of ulcer comprising the modified polypeptide of claim 3 and a pharmaceutically acceptable carrier or diluent.

9. The modified polypeptide according to claim 1, wherein $R_1$ represents a cholesteryl group which is substituted with a substituent selected from the group consisting of alkyl, alkenyl, hydroxyl and alkoxyl.

10. The method according to claim 4, wherein $R_1$ represents a cholesteryl group which is substituted with a substituent selected from the group consisting of alkyl, alkenyl, hydroxyl and alkoxyl.

11. The reactive derivative according to claim 6, wherein $R_1$ represents a cholesteryl group which is substituted with a substituent selected from the group consisting of alkyl, alkenyl, hydroxyl and alkoxyl.

12. A pharmaceutical composition comprising the modified polypeptide according to claim 1 and a pharmaceutically acceptable carrier or diluent.

* * * * *